United States Patent [19]

Lam

[11] Patent Number: 4,885,365

[45] Date of Patent: Dec. 5, 1989

[54] DITHIOCARBANATE LUBRICANT COMPOSITIONS

[75] Inventor: William Y. Lam, Ballwin, Mo.

[73] Assignee: Ethyl Petroleum Additives, Inc., St. Louis, Mo.

[21] Appl. No.: 196,507

[22] Filed: May 20, 1988

[51] Int. Cl.$^4$ ............... C07D 265/30; C07D 241/04; C07D 211/60; C07C 155/08

[52] U.S. Cl. .......................... 544/161; 558/236; 544/389; 546/245

[58] Field of Search ............... 558/236; 544/161, 389; 546/245

[56] References Cited

U.S. PATENT DOCUMENTS

| | | | |
|---|---|---|---|
| 3,462,368 | 8/1969 | Wollensak et al. | 558/236 |
| 3,778,460 | 12/1973 | Wollensak et al. | 558/236 |
| 3,833,496 | 9/1974 | Malec | 558/236 |
| 4,360,438 | 11/1982 | Rowan et al. | 558/236 |
| 4,747,965 | 5/1988 | Wollenberg et al. | 558/236 |
| 4,758,362 | 7/1988 | Butke | 558/236 |

OTHER PUBLICATIONS

Kuehle et al., Chem. Abs., vol. 62, 62:454d (1965).

Primary Examiner—Mary C. Lee
Assistant Examiner—Robert C. Whittenbaugh
Attorney, Agent, or Firm—David M. Bunnell

[57] ABSTRACT

Compounds having the formula:

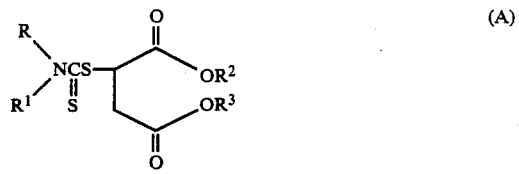

(A)

wherein:
a. R is an organic radical selected from an alkyl group, an alkenyl group, an aryl group or an aralkyl group in which the alkyl or alkenyl groups contain up to 32 carbon atoms and the aryl or aralkyl groups contain up to 15 carbon atoms;
b. $R^1$ is hydrogen or an organic radical selected from an alkyl group or alkenyl group, an aryl or aralkyl group in which the alkyl or alkenyl groups contain up to 32 carbon atoms and the aryl or aralkyl groups contain up to 15 carbon atoms;
c. $R^2$ and $R^3$ are the same or different alkyl groups containing from 1 to 32, more preferably 4 to 8, carbon atoms each are effective antiwear and antioxidant additives in lubricating oil.

3 Claims, No Drawings

DITHIOCARBANATE LUBRICANT COMPOSITIONS

BACKGROUND OF THE INVENTION

This invention relates to certain dihydrocarbyl-N-hydrocarbyl-2-(dithiocarbamyl)succinate and dihydrocarbyl-N,N-dihydrocarbyl-2-(dithiocarbamyl)succinate products having utility as lubricant additives and lubricating compositions containing them. The invention also relates to a process for preparing such products.

Additives are conventionally added to lubricating oils to improve their properties. Antiwear additives used in the past include compounds such as zinc dialkyldithiophosphates, sulfurized sperm oil, and the like. Antioxidant additives used in the past include sulfurized oil-soluble organic compounds, such as wax sulfides and polysulfides, sulfurized olefins, sulfurized fatty acid esters, and sulfurized olefin esters, as well as oil-soluble phenolic and aromatic amine antioxidants.

It has now been found that certain dihydrocarbyl-N-hydrocarbyl-2-(dithiocarbamyl)succinate and dihydrocarbyl-N,N-dihydrocarbyl-2-(dithiocarbamyl)succinate products are very effective antiwear and antioxidant additives in lubricating compositions such as crankcase lubricants.

DETAILED DESCRIPTION OF THE INVENTION

Accordingly, in one aspect of the present invention there is provided an antiwear and antioxidant compound having the general formula:

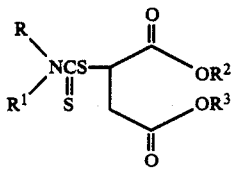
(A)

wherein:
a. R is an organic radical selected from an alkyl group, an alkenyl group, an aryl group or an aralkyl group in which the alkyl or alkenyl groups contain up to 32 carbon atoms and the aryl or aralkyl groups contain up to 15 carbon atoms;
b. $R^1$ is hydrogen or an organic radical selected from an alkyl group or alkenyl group, an aryl or aralkyl group in which the alkyl or alkenyl groups contain up to 32 carbon atoms and the aryl or aralkyl groups contain up to 15 carbon atoms; and,
c. $R^2$ and $R^3$ are the same or different alkyl groups containing from 1 to 32 carbon atoms each.

Representative examples of the above compounds include:
dimethyl-N-methyl-2-(dithiocarbamyl)succinate;
dimethyl-N-ethyl-2-(dithiocarbamyl)succinate;
dimethyl-N-n-propyl-2-(dithiocarbamyl)succinate;
dimethyl-N-isopropyl-2-(dithiocarbamyl)succinate;
dimethyl-N-n-butyl-2-(dithiocarbamyl)succinate;
dimethyl-N-sec-butyl-2-(dithiocarbamyl)succinate;
dimethyl-N-cyclohexyl-2-(dithiocarbamyl)succinate;
dimethyl-N-eicosyl-2-(dithiocarbamyl)succinate;
dimethyl-N-chlorobenzyl-2-(dithiocarbamyl)succinate;
dimethyl-N-nitrobenzyl-2-(dithiocarbamyl)succinate;
dimethyl-N-2-ethoxyethyl-2-(dithiocarbamyl)succinate;
dimethyl-N-4-carbomethoxyhexyl-2-(dithiocarbamyl)succinate;
dimethyl-N-phenyl-2-(dithiocarbamyl)succinate;
dimethyl-N-o-toluyl-2-(dithiocarbamyl)succinate;
dimethyl-N-m-toluyl-2-(dithiocarbamyl)succinate;
dimethyl-N-2,4-xylyl-2-(dithiocarbamyl)succinate;
dimethyl-N-3-propylphenyl-2-(dithiocarbamyl)succinate;
dimethyl-N-4-aminophenyl-2-(dithiocarbamyl)succinate;
dimethyl-N-2,6-diaminonaphthyl-2-(dithiocarbamyl)succinate;
dimethyl-N-2-methoxyethyl-2-(dithiocarbamyl)succinate;
dimethyl-N-ethylsulfide-2-(dithiocarbamyl)succinate;
diethyl-N-methyl-2-(dithiocarbamyl)succinate;
diethyl-N-isopropyl-2-(dithiocarbamyl)succinate;
diethyl-N-sec-butyl-2-(dithiocarbamyl)succinate;
diethyl-N-cyclohexyl-2-(dithiocarbamyl)succinate;
diethyl-N-eicosyl-2-(dithiocarbamyl)succinate;
diethyl-N-phenyl-2-(dithiocarbamyl)succinate;
diethyl-N-diaminonaphthyl-2-(dithiocarbamyl)succinate;
diisopropyl-N-methyl-2-(dithiocarbamyl)succinate;
diisopropyl-N-sec-butyl-2-(dithiocarbamyl)succinate;
diisopropyl-N-phenyl-2-(dithiocarbamyl)succinate;
dibutyl-N-methyl-2-(dithiocarbamyl)succinate;
dibutyl-N-ethyl-2-(dithiocarbamyl)succinate;
dibutyl-N-sec-butyl-2-(dithiocarbamyl)succinate;
dibutyl-N-octyl-2-(dithiocarbamyl)succinate;
dibutyl-N-3-propylphenyl-2-(dithiocarbamyl)succinate;
dipentyl-N-methyl-2-(dithiocarbamyl)succinate;
dipentyl-N-isopropyl-2-(dithiocarbamyl)succinate;
dipentyl-N-dodecyl-2-(dithiocarbamyl)succinate;
dipentyl-N-2-methoxyethyl-2-(dithiocarbamyl)succinate;
dihexyl-N-methyl-2-(dithiocarbamyl)succinate;
dihexyl-N-n-butyl-2-(dithiocarbamyl)succinate;
dihexyl-N-octyl-2-(dithiocarbamyl)succinate;
dihexyl-N-dodecyl-2-(dithiocarbamyl)succinate;
dioctyl-N-methyl-2-(dithiocarbamyl)succinate;
dioctyl-N-isopropyl-2-(dithiocarbamyl)succinate;
dioctyl-N-m-toluyl-2-(dithiocarbamyl)succinate;
didodecyl-N-methyl-2-(dithiocarbamyl)succinate;
didodecyl-N-octyl-2-(dithiocarbamyl)succinate;
didodecyl-N-eicosyl-2-(dithiocarbamyl)succinate;
dieicosyl-N-methyl-2-(dithiocarbamyl)succinate;
ditriacontanyl-N-methyl-2-(dithiocarbamyl)succinate;
dimethyl-N,N-dimethyl-2-(dithiocarbamyl)succinate;
dimethyl-N,N-diethyl-2-(dithiocarbamyl)succinate;
dimethyl-N,N-diisopropyl-2-(dithiocarbamyl)succinate;
dimethyl-N,N-di-n-butyl-2-(dithiocarbamyl)succinate;
dimethyl-N,N-di-sec-butyl-2-(dithiocarbamyl)succinate;
dimethyl-N,N-dipentyl-2-(dithiocarbamyl)succinate;
dimethyl-N,N-dihexyl-2-(dithiocarbamyl)succinate;
dimethyl-N,N-dioctyl-2-(dithiocarbamyl)succinate;
dimethyl-N,N-didodecyl-2-(dithiocarbamyl)succinate;
dimethyl-N,N-dieicosyl-2-(dithiocarbamyl)succinate;
dimethyl-N,N-ditriacontanyl-2-(dithiocarbamyl)succinate;
dimethyl-N,N-dichlorobenzyl-2-(dithiocarbamyl)succinate;
dimethyl-N,N-dinitrobenzyl-2-(dithiocarbamyl)succinate;
dimethyl-N,N-diphenyl-2-(dithiocarbamyl)succinate;
dimethyl-N,N-p-ditolyl-2-(dithiocarbamyl)succinate;
dimethyl-N,N-2,4-dixylyl-2-(dithiocarbamyl)succinate;

diethyl-N,N-dimethyl-2-(dithiocarbamyl)succinate;
diethyl-N,N-diisopropyl-2-(dithiocarbamyl)succinate;
diethyl-N,N-di-n-butyl-2-(dithiocarbamyl)succinate;
diethyl-N,N-di-sec-butyl-2-(dithiocarbamyl)succinate;
diethyl-N,N-dipentyl-2-(dithiocarbamyl)succinate;
diethyl-N,N-dioctyl-2-(dithiocarbamyl)succinate;
diethyl-N,N-didodecyl-2-(dithiocarbamyl)succinate;
diethyl-N,N-dieciosyl-2-(dithiocarbamyl)succinate;
diethyl-N,N-diphenyl-2-(dithiocarbamyl)succinate;
diethyl-N,N-bis(2,6-diaminonaphthyl)-2-(dithiocarbamyl)succinate;
diisopropyl-N,N-dimethyl-2-(dithiocarbamyl)succinate;
diisopropyl-N,N-diethyl-2-(dithiocarbamyl)succinate;
diisopropyl-N,N-dibutyl-2-(dithiocarbamyl)succinate;
diisopropyl-N,N-dioctyl-2-(dithiocarbamyl)succinate;
diisopropyl-N,N-didodecyl-2-(dithiocarbamyl)succinate;
di-n-butyl-N,N-dimethyl-2-(dithiocarbamyl)succinate;
di-n-butyl-N,N-diisopropyl-2-(dithiocarbamyl)succinate;
di-sec-butyl-N,N-diheptyl-2-(dithiocarbamyl)succinate;
di-sec-butyl-N,N-dioctyl-2-(dithiocarbamyl)succinate;
di-tert-butyl-N,N-didodecyl-2-(dithiocarbamyl)succinate;
di-tert-butyl-N,N-3-propylphenyl-2-(dithiocarbamyl)succinate;
dipentyl-N,N-dimethyl-2-(dithiocarbamyl)succinate;
dipentyl-N,N-diisopropyl-2-(dithiocarbamyl)succinate;
dipentyl-N,N-dihexyl-2-(dithiocarbamyl)succinate;
dipentyl-N,N-dioctyl-2-(dithiocarbamyl)succinate;
dipentyl-N,N-didodecyl-2-(dithiocarbamyl)succinate;
dipentyl-N,N-dioctadecyl-2-(dithiocarbamyl)succinate;
dioctyl-N,N-dimethyl-2-(dithiocarbamyl)succinate;
dioctyl-N,N-dipentyl-2-(dithiocarbamyl)succinate;
dioctyl-N,N-didodecyl-2-(dithiocarbamyl)succinate;
dioctyl-N,N-2,4-dixylyl-2-(dithiocarbamyl)succinate;
didodecyl-N,N-dimethyl-2-(dithiocarbamyl)succinate;
didodecyl-N,N-diheptyl-2-(dithiocarbamyl)succinate;
dieciosyl-N,N-dimethyl-2-(dithiocarbamyl)succinate;
dieciosyl-N,N-isopropyl-2-(dithiocarbamyl)succinate;
ditriacontanyl-N,N-dimethyl-2-(dithiocarbamyl)succinate;
dimethyl-N-methyl-N-ethyl-2-(dithiocarbamyl)succinate;
dimethyl-N-methyl-N-isopropyl-2-(dithiocarbamyl)succinate;
dimethyl-N-methyl-N-octyl-2-(dithiocarbamyl)succinate;
dimethyl-N-methyl-N-octadecyl-2-(dithiocarbamyl)succinate;
dimethyl-N-ethyl-N-hexyl-2-(dithiocarbamyl)succinate;
dimethyl-N-methyl-N-phenyl-2-(dithiocarbamyl)succinate;
dimethyl-N-isopropyl-N-2,6-diaminonaphthyl-2-(dithiocarbamyl)succinate;
dimethyl-N-ethyl-N-dodecyl-2-(dithiocarbamyl)succinate;
diethyl-N-methyl-N-isopropyl-2-(dithiocarbamyl)succinate;
diethyl-N-methyl-N-hexyl-2-(dithiocarbamyl)succinate;
diethyl-N-methyl-N-octadecyl-2-(dithiocarbamyl)succinate;
diethyl-N-isopropyl-N-dodecyl-2-(dithiocarbamyl)succinate;
diethyl-N-isopropyl-N-phenyl-2-(dithiocarbamyl)succinate;
diisopropyl-N-methyl-N-ethyl-2-(dithiocarbamyl)succinate;
diisopropyl-N-methyl-N-isopropyl-2-(dithiocarbamyl)succinate;
diisopropyl-N-ethyl-N-hexyl-2-(dithiocarbamyl)succinate;
diisopropyl-N-methyl-N-phenyl-2-(dithiocarbamyl)succinate;
dibutyl-N-methyl-N-ethyl-2-(dithiocarbamyl)succinate;
dibutyl-N-methyl-N-octadecyl-2-(dithiocarbamyl)succinate;
dibutyl-N-ethyl-N-dodecyl-2-(dithiocarbamyl)succinate;
dibutyl-N-ethyl-N-2,6-diaminonaphthyl-2-(dithiocarbamyl)succinate;
dioctyl-N-methyl-N-ethyl-2-(dithiocarbamyl)succinate;
dioctyl-N-ethyl-N-isopropyl-2-(dithiocarbamyl)succinate;
dioctyl-N-sec-butyl-N-dodecyl-2-(dithiocarbamyl)succinate;
didodecyl-N-methyl-N-ethyl-2-(dithiocarbamyl)succinate;
didodecyl-N-methyl-N-isopropyl-2-(dithiocarbamyl)succinate; and the like.

The additives of the invention are readily prepared by reacting a primary or secondary amine, i.e. compounds having one or more primary or secondary amino groups, preferably primary or secondary monoamines having the general formula:

$$R-NH-R^1$$

wherein R and $R^1$ are as defined above with carbon disulfide and a dialkyl maleate having the general formula:

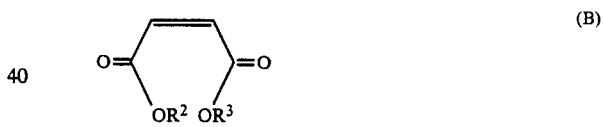

(B)

wherein $R^2$ and $R^3$ are as hereinbefore defined.

As stated above, the amine reactants of the present invention can be represented by the general formula:

$$R-NH-R^1$$

where R is an organic radical, e.g. an alkyl group, an alkenyl group, an aryl group, or an aralkyl group. The alkyl or alkenyl groups can contain up to 32 carbon atoms, preferably up to 12 carbon atoms, and the aryl or aralkyl groups, which include a benzene or a naphthalene nucleus substituted by alkyl radicals or aryl or aralkyl radicals, preferably contain up to 15 carbon atoms each. The alkyl or alkenyl groups can be acyclic and of straight chain or branched structure, or they may be alicyclic. The R group may be interrupted by a hetero atom linkage, such as O or S, and may contain one or more primary or secondary amino groups. In the foregoing formula, $R^1$ can be hydrogen, but it may be an alkyl, alkenyl, aryl or aralkyl group, as defined for R, and may be the same as R or it may be different from R in a given compound. When R and $R^1$ are alkyl groups, they may be joined together to form a heterocyclic link with the nitrogen atom to which they are attached. R and $R^1$ may also be substituted by noninterfering groups such as alkoxy, halo and amido groups, and the like.

Specific examples of suitable amine reactants which can be used in the practice of the present invention include methylamine, ethylamine, propylamine, isopropylamine, n-butylamine, sec-butylamine, isobutylamine, pentylamine, hexylamine, cyclohexylamine, heptylamine, octylamine, dodecylamine, octadecylamine, eicosylamine, triacontanylamine, benzylamine, chlorobenzylamine, nitrobenzylamine, 2-ethoxyethylamine, 4-carbomethoxyhexylamine, dimethylamine, diethylamine, di-n- propylamine, diisopropylamine, di-n-butylamine, di-sec-butylamine, diisobutylamine, di-tert-butylamine, dipentylamine, dihexylamine, dioctylamine, dieicosylamine, ditriacontanylamine, N-methylethylamine, N-methylpropylamine, N-methyloctadecylamine, N-ethylhexylamine, N-ethyldodecylamine, N-propyldodecylamine, aniline, toluidine (o-, m-, or p-), 2,4-xylidine, 3,4-xylidine, 2,5-xylidine, 4-ethylaniline, 3-propylaniline, 1,3-diamino benzene, 4,4,-diamino-diphenyl methane, p-chloro aniline, 2,6-diamino toluene, 4,4,-diaminodiphenyl, 2,4,4,-triamino diphenyl ether, 2,6-diamino naphthalene, 1,5-diamino-2-methylpentane, phenylethyl amine, piperidine, morphol-ine, piperazine, glycine, 2-amino ethyl ether, 2-amino ethyl sulfide, and the like. The preferred amino compounds are lower alkyl secondary amines wherein each of R and $R^1$ as described above have up to about 12 carbon atoms.

Specific examples of suitable dialkyl maleate reactants which can be used in the practice of the present invention include dimethyl maleate, diethyl maleate, dipropyl maleate, dibutyl maleate, dipentyl maleate, dihexyl maleate, diheptyl maleate, dioctyl maleate, dodecyl maleate, didodecyl maleate, dioctadecyl maleate, dieicosyl maleate, ditriacontanyl maleate, methylethyl maleate, methyl-n-propyl maleate, methylisobutyl maleate, ethylhexyl maleate, ethyloctyl maleate, ethyldodecyl maleate, ethyleicosyl maleate, n-butylheptyl maleate, pentyl octyl maleate, hexyldecyl maleate, octyldecyl maleate, dicyclohexyl maleate, dicyclododecyl maleate and the like, and the isomeric forms thereof.

The dialkyl maleate esters used in the practice of the present invention are well-known compounds as are methods for their preparation. For example, they can be prepared by heating maleic anhydride or maleic acid with the alkanol of choice, typically in the presence of an acid catalyst such as sulfuric acid or toluenesulfonic acid or by reacting a halide of maleic acid with the desired alkanol.

In the practice of the present invention, the reactants are employed in approximately equal mole quantities although this limitation is not critical. Typically, a slight excess of carbon disulfide is used to compensate for any loss of carbon disulfide which may occur through volatilization during the course of the reaction to insure maximum product yield. The reaction can be conveniently carried out by merely mixing and heating the reactants. It is preferred, however, to add the amine reactant to a mixture of the carbon disulfide and maleate reactants slowly, in a dropwise fashion, so as to suppress unwanted amine salt formation which can occur if the carbon disulfide and amine reactants are brought into immediate contact.

In general, a reaction temperature should be used which is high enough to promote the reaction at a reasonable rate, but not so high as to cause decomposition. A useful range is from about 30°–100° C. A more useful range is from about 50°–90 °C.

The reaction can be carried out in an inert atmosphere, if desired, but the use of an inert atmosphere above the reaction mixture is not required.

The reaction should be carried out for a time sufficient to form a substantial amount of product. This is usually accomplished in from 0.5 to 12 hours. A more useful time range is from about 2 to 4 hours.

Thus, in accordance with another aspect of the invention, there is provided a process for preparing an oil-soluble compound having the general formula:

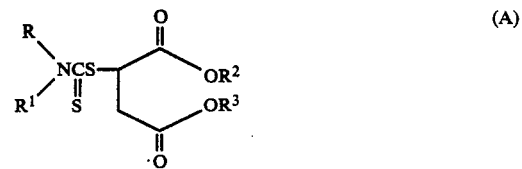

(A)

wherein:
a. R is an organic radical selected from an alkyl group, an alkenyl group, an aryl group or an aralkyl group in which the alkyl or alkenyl groups contain up to 32 carbon atoms and the aryl or aralkyl groups contain up to 15 carbon atoms;
b. $R^1$ is hydrogen or an organic radical selected from an alkyl group or alkenyl group, an aryl or aralkyl group in which the alkyl or alkenyl groups contain up to 32 carbon atoms and the aryl or aralkyl groups contain up to 15 carbon atoms; and,
c. $R^2$ and $R^3$ are alkyl groups containing from 1 to 12 carbon atoms, which comprises reacting an amine having the general formula:

$$R-NH-R^1$$

wherein R is an organic radical selected from an alkyl group, an alkenyl group, an aryl group or an aralkyl group in which the alkyl or alkenyl groups contain up to 32 carbon atoms and the aryl or aralkyl groups contain up to 15 carbon atoms each and $R^1$ is hydrogen or an organic radical selected from an alkyl group or alkenyl group, an aryl group or an aralkyl group in which the alkyl or alkenyl groups contain up to 32 carbon atoms and the aryl or aralkyl groups contain up to 15 carbon atoms each with carbon disulfide and a dialkyl maleate having the general formula:

(B)

wherein $R^2$ and $R^3$ are the same or different alkyl groups containing from 1 to 12 carbon atoms each.

Preferably, the lubricating compositions of the present invention comprise from 0.1% to 10%, more preferably from 0.25% to 5%, by weight of the oil-soluble compounds of the foregoing formula (A) and the lubricating oil may be any of the well-known mineral or synthetic oils of appropriate viscosity characteristics.

It will be understood that lubricating compositions of the present invention may also contain, if desired, conventional lubricant additives such as ancillary antioxidants and antiwear additives (preferably ashless), corrosion inhibitors, dispersants, detergents, thickeners, pour-point depressants and viscosity index improvers.

Hence, in accordance with a further embodiment of the present invention, there is provided a lubricating composition containing a major amount of lubricating oil and a minor antiwear-antioxidant amount of a compound having the general formula:

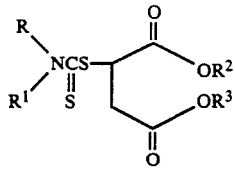

(A)

wherein:
a. R is an organic radical selected from an alkyl group, an alkenyl group, an aryl group or an aralkyl group in which the alkyl or alkenyl groups contain up to 32 carbon atoms and the aryl or aralkyl groups contain up to 15 carbon atoms;
b. $R^1$ is hydrogen or an organic radical selected from an alkyl group or alkenyl group, an aryl or aralkyl group in which the alkyl or alkenyl groups contain up to 32 carbon atoms and the aryl or aralkyl groups contain up to 15 carbon atoms; and,
c. $R^2$ and $R^3$ are the same or different alkyl groups containing from 1 to 12 carbon atoms each.

The additives of the present invention may also be conveniently prepared as a concentrate consisting of a concentrated solution of a major amount of the additives and a minor amount of a mineral or synthetic lubricating oil, or as an additive package consisting of a concentrated solution in mineral oil or synthetic oil of a major amount of a combination of the additives with one or more conventional additives. Such concentrates and packages are frequently very convenient forms in which to handle and transport additives and are diluted with further quantities of oil, and optionally blended with further additives, before use.

Thus, in accordance with a further aspect of the invention, there is provided a solution comprising a major amount of one or more compounds having the formula (A) and a minor amount of a lubricating oil. One or more conventional additives may be combined with the compounds of formula (A).

The following examples serve to illustrate the manner in which the antiwear-antioxidant additives are prepared but not to limit in any respect the scope of the invention claimed.

EXAMPLE I

To a 250 milliliter reaction vessel equipped with a stirrer, thermometer and condenser was added 28.8 grams (0.2 mole) of dimethyl maleate and 17.6 grams (0.23 mole) of carbon disulfide. Diisopropylamine (20.2 grams; 0.2 mole) was added slowly at 19° C. The reaction temperature immediately began to rise and a yellow solution was formed. Later, a crystalline solid was formed in the liquid reaction mixture. After 20 minutes, all of the amine had been added and the temperature had reached 61° C. The reaction mixture was heated to 70° C. at which time the solid melted and was maintained at 70° C. for 1 hour. The resulting product was dissolved in heptane and the solution was washed with aqueous sodium hydroxide, dilute hydrochloric acid, and a sodium chloride solution. The solvent was removed under vacuum at 70° C. to give a yellow liquid which was then filtered. The product was a yellow fluid (approximately 58.0 grams) having good solubility in mineral oil and heptane. Analysis by NMR served to identify the product as dimethyl-N,N-diisopropyl-2-(dithiocarbamyl)succinate.

EXAMPLE II

To a 250 milliliter reaction vessel equipped with a stirrer, thermometer and condenser was added 45.6 grams (0.2 mole) of dibutyl maleate and 26.9 grams (0.35 mole) of carbon disulfide. Diisopropylamine (20.2 grams; 0.2 mole) was added slowly to the mixture. The temperature began to rise as a yellow liquid was formed. A crystalline solid was later formed along the reactor walls and some in the liquid reaction medium. After all of the amine was added in about 12 minutes, the temperature reached 70° C. where it was maintained for about 1 hour. The resulting product was dissolved in heptane and the solution was washed with aqueous sodium hydroxide, dilute hydrochloric acid and water. The solvent was removed under vacuum at 70° C. to give a yellow liquid product (approx. 76.0 grams) which was filtered. Analysis by NMR served to identify the products as dibutyl-N,N-diisopropyl-2-(dithiocarbamyl)succinate.

EXAMPLE III

To a 250 milliliter reaction vessel equipped with a stirrer, thermometer and condenser containing a mixture of 34.4 grams (0.2 mole) of diethyl maleate and 17.3 grams (0.23 mole) of carbon disulfide there was added slowly 25.8 grams (0.2 mole) of di-n-butylamine at room temperature. The temperature started to rise as a yellow liquid was formed. Some crystalline solid was formed as the amine reached the vessel wall and reacted with carbon disulfide vapor. After all of the amine was added in about 22 minutes, the temperature had reached 71° C. where it was maintained for about 1 hour. The resulting material was dissolved in heptane and the solution was washed with dilute hydrochloric acid and water. Removal of solvent under vacuum at 70° C. gave a liquid (approximately 72.4 grams) which was filtered. Analysis by NMR served to identify the product as diethyl-N,N-di-n-butyl-2-(dithiocarbamyl)succinate.

EXAMPLE IV

To a 1 liter reaction vessel equipped with a stirrer, thermometer and condenser was added 253.7 grams (1.11 mole) of dibutyl maleate and 78.0 grams (1.03 mole) of carbon disulfide and the mixture was heated gradually to 90° C., however, the reaction temperature stabilized at 72°–73° C. Di-n-butylamine (129.3 grams; 1.0 mole) was added dropwise to the reaction mixture over a period of about 25 to 30 minutes. The temperature rose gradually to 113° C. where it remained until the amine addition was completed. The reaction mixture was then maintained at 90°–113° C. for 1 hour. Vacuum was applied to strip off volatiles at 30° C. for 30 minutes. An orange fluid product (453.7 grams) was collected without filtration. Analysis by NMR served to identify the product as di-n-butyl-N,N-di-n-butyl-2-(dithiocarbamyl)succinate.

The antiwear properties of the lubricating oil compositions of the present invention were determined in a 4-Ball Wear Test. This test is conducted in a device comprising four steel balls, three of which are in contact with each other in one plane in a fixed triangular position and a reservoir containing the test sample. The fourth ball is above and in contact with the other three. In conducting the test, the upper ball is rotated while it is pressed against the other three balls while pressure is applied by weight and lever arms. The diameter of the scar on the three lower balls is measured by means of a low-power microscope, and the average diameter measured in two directions on each of three lower balls is taken as a measure of the antiwear characteristics of the oil. A larger scar diameter means more wear. The balls were immersed in base lube oil containing the test additives. Applied load was 20 kg and rotation was at 1800 rpm for 60 minutes at 130° F. Tests were conducted with both base oil alone (Exxon 90W mineral oil) and with base oil containing the additives of Examples I, II and III. The following results were obtained:

| Oil Formulation | Scar Diameter (mm) |
|---|---|
| Base Oil | 0.718 |
| Base Oil + 0.58 wt. % additive (Example I) | 0.375 |
| Base Oil + 0.77 wt. % additive (Example II) | 0.350 |
| Base Oil + 0.74 wt. % additive (Example III) | 0.337 |

The results in the table show that lubricating oil containing the additive products of the present invention gave a scar diameter significantly less than base oil alone.

Hot Oil Oxidation Tests were carried out to demonstrate the antioxidant effectiveness of the present additives. In these tests, fully formulated mineral lubricating oil samples were prepared both with and without the additive. The oil was placed in a test cell together with 0.3 cubic centimeter of a catalyst composition prepared by dissolving 6.65 grams of ferric acetylacetonate and 0.6 gram of cupric acetylacetonate in 100 grams of xylene. The cell was heated to 160° C. and dry air blown through the heated oil for 48 hours at a rate of 10 liters/hour. The percent viscosity increase was measured at 40° C. The following results were obtained:

| Additive | Percent Viscosity Increase |
|---|---|
| None | 124.4 |
| Example IV (0.31 wt. % based on total weight of the oil) | 82.0 |

Another Hot Oil Oxidation Test was carried out in a fully formulated mineral lubricating oil containing the additive product of Example IV following the same procedure described above with the exception that the test was run for 64 hours instead of 48 hours. The following results were obtained.

| Additive | Percent Viscosity Increase |
|---|---|
| None | 1505 |
| Example IV (0.8 wt. % based on total weight of the oil) | 515 |
| Example IV (1.2 wt. % based on total weight of the oil) | 278.6 |

These results demonstrate that the additives of the invention are very effective antioxidants.

What is claimed:

1. Compounds having the formula:

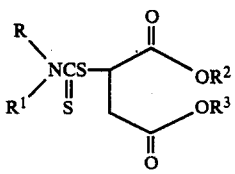

wherein:
a. R is an organic radical selected from an aryl group consisting of a benzene or a naphthalene group or an aralkyl group wherein the aryl portion is selected from benzene or naphthalene in which the aryl or aralkyl groups contain up to 15 carbon atoms;
b. $R^1$ is hydrogen or an organic radical selected from an alkyl group, an alkenyl group, an aryl group consisting of a benzene or a naphthalene group or an aralkyl group consisting of an alkylbenzene or an alkylnaphthalene in which the alkyl or alkenyl groups contain up to 32 carbon atoms and the aryl or aralkyl groups contain up to 15 carbon atoms; or
c. R and $R^1$ together with the nitrogen atom to which they are attached form a heterocyclic moiety selected from the group consisting of piperidine, morpholine and piperazine; and,
d. $R^2$ and $R^3$ are the same or different alkyl groups containing from 1 to 32 carbon atoms each.

2. The compound of claim 1 wherein both R and $R^1$ are selected from an aryl group or an aralkyl group.

3. The compound of claim 1 wherein R and $R^1$ together with the nitrogen to which they are attached form a heterocyclic moiety selected from the group consisting of piperidine, morpholine, and piperazine.

* * * * *